(12) United States Patent
Hamamoto

(10) Patent No.: US 10,211,390 B2
(45) Date of Patent: Feb. 19, 2019

(54) FRICTION DRIVE ACTUATOR

(71) Applicant: Sharp Kabushiki Kaisha, Osaka (JP)

(72) Inventor: Masaki Hamamoto, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 249 days.

(21) Appl. No.: 15/110,117

(22) PCT Filed: Nov. 17, 2014

(86) PCT No.: PCT/JP2014/080294
§ 371 (c)(1),
(2) Date: Jul. 7, 2016

(87) PCT Pub. No.: WO2015/125359
PCT Pub. Date: Aug. 27, 2015

(65) Prior Publication Data
US 2016/0351786 A1 Dec. 1, 2016

(30) Foreign Application Priority Data

Feb. 18, 2014 (JP) .................. 2014-028895

(51) Int. Cl.
*H01L 41/09* (2006.01)
*H02N 2/00* (2006.01)
(Continued)

(52) U.S. Cl.
CPC ........ *H01L 41/0906* (2013.01); *A61B 1/0016* (2013.01); *A61B 1/00078* (2013.01);
(Continued)

(58) Field of Classification Search
CPC ....... H02N 2/02; H02N 2/004; H01L 41/0906
See application file for complete search history.

(56) References Cited

U.S. PATENT DOCUMENTS

| | | | | |
|---|---|---|---|---|
| 5,453,653 A | * | 9/1995 | Zumeris | H01L 41/0913 310/315 |
| 7,309,943 B2 | * | 12/2007 | Henderson | G02B 7/102 310/323.02 |

(Continued)

FOREIGN PATENT DOCUMENTS

| JP | H02311184 A | 12/1990 |
|---|---|---|
| JP | H05-337127 A | 12/1993 |

(Continued)

OTHER PUBLICATIONS

International Search Report of PCT/JP2014/080294 dated Jan. 27, 2015.

(Continued)

*Primary Examiner* — J. San Martin
(74) *Attorney, Agent, or Firm* — ScienBiziP, P.C.

(57) ABSTRACT

Provided is a friction drive actuator that is resistant to contamination of, for example, extraneous matter. An ultrasonic actuator according to an aspect of the present invention drives a columnar insertion section and includes a columnar vibrating body (40), whose distal end is pressed against a side surface of the insertion section, and a piezoelectric element (44), an upper electrode (44*a*), and a lower electrode (44*b*) that are provided at one side surface of the vibrating body.

12 Claims, 13 Drawing Sheets

(51) Int. Cl.
  *H02N 2/02* (2006.01)
  *A61B 1/00* (2006.01)
  *A61B 1/313* (2006.01)

(52) U.S. Cl.
  CPC .......... *A61B 1/3132* (2013.01); *H02N 2/004* (2013.01); *H02N 2/0095* (2013.01); *H02N 2/02* (2013.01); *H02N 2/026* (2013.01); *A61B 1/00147* (2013.01)

(56) References Cited

U.S. PATENT DOCUMENTS

| | | | | |
|---|---|---|---|---|
| 7,312,559 | B2* | 12/2007 | Lee | ...................... H02N 2/0015 310/323.01 |
| 7,382,080 | B2* | 6/2008 | Lee | ...................... H02N 2/0015 310/316.01 |
| 8,445,837 | B2* | 5/2013 | Matsukawa | .............. G02B 7/08 250/239 |
| 8,698,374 | B2* | 4/2014 | Xu | ........................ H02N 2/0015 310/317 |
| 2003/0208187 | A1 | 11/2003 | Layer | |
| 2003/0208207 | A1 | 11/2003 | Layer | |
| 2004/0027032 | A1 | 2/2004 | Moteki et al. | |
| 2005/0234435 | A1 | 10/2005 | Layer | |
| 2006/0043824 | A1* | 3/2006 | Sakano | .................. G02B 7/102 310/323.09 |
| 2007/0236106 | A1 | 10/2007 | Koc et al. | |
| 2008/0103358 | A1 | 5/2008 | Suzuki | |
| 2009/0261690 | A1* | 10/2009 | Mashimo | .................. A61B 8/12 310/323.03 |
| 2009/0278421 | A1 | 11/2009 | Hamamoto et al. | |
| 2011/0245844 | A1 | 10/2011 | Jinno | |

FOREIGN PATENT DOCUMENTS

| | | | |
|---|---|---|---|
| JP | H09-56667 | 3/1997 | |
| JP | H09-140663 | 6/1997 | |
| JP | 2000-157485 A | 6/2000 | |
| JP | 2005-5244-40 A | 8/2005 | |
| JP | 2005-270171 A | 10/2005 | |
| JP | 2005-328697 A | 11/2005 | |
| JP | 2007275885 A | 10/2007 | |
| JP | 2008-283756 | 11/2008 | |
| JP | 2009-018044 A | 1/2009 | |
| JP | 2009-153283 | 7/2009 | |
| JP | 2009-278702 A | 11/2009 | |
| JP | 2011-206312 A | 10/2011 | |
| JP | 2013183563 A | 9/2013 | |
| WO | WO2008038817 A1 | 4/2008 | |
| WO | 2015/125359 A1 | 8/2015 | |
| WO | WO 2016012020 A1 * | 1/2016 | ........... H01L 41/083 |

OTHER PUBLICATIONS

International Search Report of PCT/JP2014/080292 dated Feb. 24, 2015.
"Catheter Insertion Module Using Friction Wheel Mechanism for Vascular Surgery" in Journal of the Japan Society of Computer Aided Surgery, vol. 15 (2013), No. 2, Special No. 22nd Annual Congress of Japan Society of Computer Aided Surgery, p. 162-163.
Co-pending letter which recites three co-pending applications U.S. Appl. Nos. 15/574,974, 15/118,274 and 15/573,518.
Restriction Requirement dated Jun. 15, 2018 against the co-pending U.S. Appl. No. 15/118,274 of the present application.

* cited by examiner

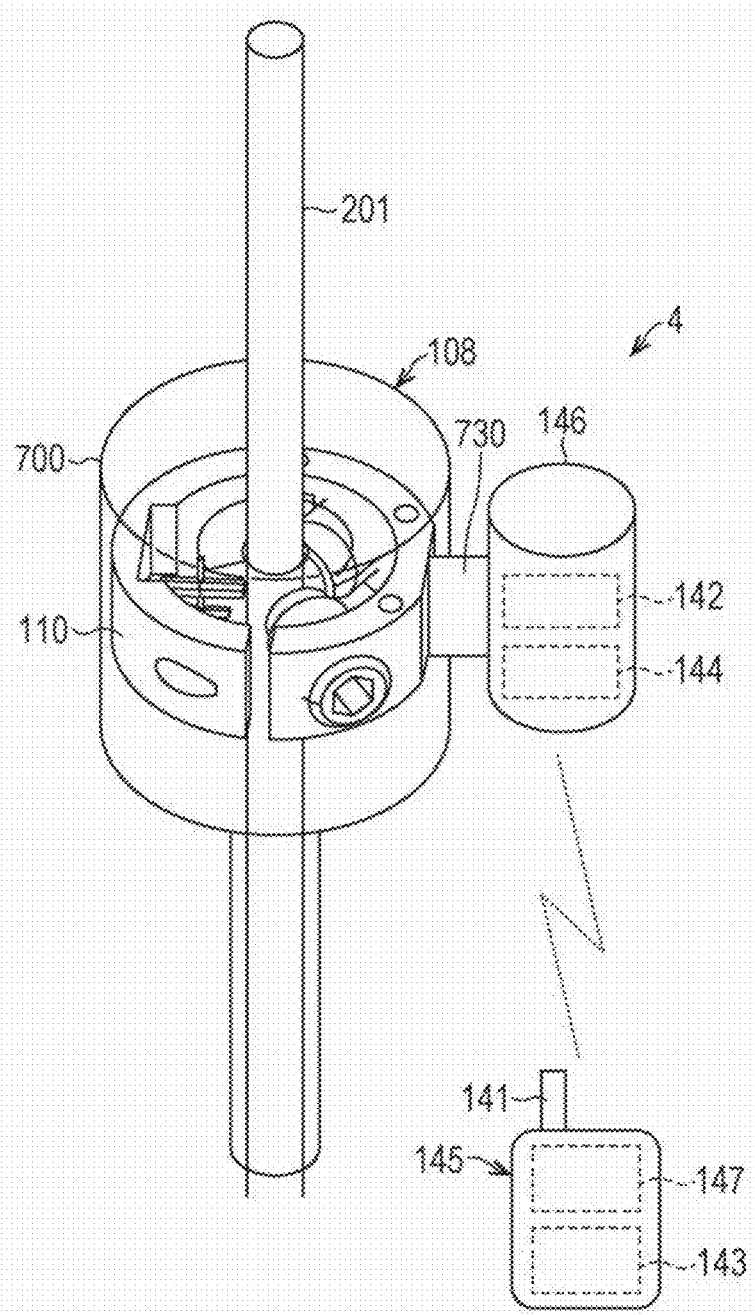

FRICTION DRIVE ACTUATOR

TECHNICAL FIELD

The present invention relates to friction drive actuators that drive operation elements by friction.

BACKGROUND ART

In the related art, ultrasonic actuators (friction drive actuators) utilizing vibration of, for example, ultrasonic waves have been used for various purposes. One example of an ultrasonic actuator vibrates, for example, a piezoelectric element with high frequency so as to drive an operation element (object) by a frictional force. Such an ultrasonic actuator is often used for driving a camera lens for focal adjustment.

Patent Literatures 1 and 2 each disclose an actuator that utilizes a traveling wave to drive a shaft (operation element) with two degrees of freedom (linear movement and rotation).

CITATION LIST

Patent Literature

PTL 1: PCT International Publication No. WO 2008/038817 (Apr. 3, 2008)
PTL 2: Japanese Unexamined Patent Application Publication No. 2013-183563 (Sep. 12, 2013)

SUMMARY OF INVENTION

Technical Problem

In the technologies according to Patent Literatures 1 and 2, a cylindrical shaft is fitted in a circular through-hole provided in a stator that generates traveling-wave vibration. Therefore, it is necessary to bring the entire circumference of the shaft and the through-hole in the stator into surface contact with each other with an error smaller than the amplitude of ultrasonic vibration. Thus, high processing precision is required with respect to the shaft and the stator. Moreover, since the entire circumference of the shaft and the through-hole in the stator have to be brought into surface contact with each other with high precision, such an actuator is vulnerable to contamination of, for example, a solid or a liquid adhered to the shaft.

For example, assuming that a rigid endoscope is to be driven by an ultrasonic actuator, it is conceivable that, for example, blood may adhere to an insertion section (shaft) of the rigid endoscope. This may conceivably cause the ultrasonic actuator to not operate.

The present invention has been made to solve the problems mentioned above, and an object thereof is to provide a friction drive actuator that is resistant to contamination of, for example, extraneous matter.

Solution to Problem

A friction drive actuator according to an aspect of the present invention drives a columnar operation element and includes a columnar vibrating body having a protrusion at a distal end thereof and a first vibration generating element and a second vibration generating element that are provided at one side surface of the vibrating body. The vibrating body is pressed against a side surface of the operation element via the protrusion.

Advantageous Effects of Invention

According to an aspect of the present invention, an operation element can be properly driven even when there is contamination of, for example, extraneous matter.

BRIEF DESCRIPTION OF DRAWINGS

FIG. 15 is a schematic diagram illustrating the schematic configuration of a medical apparatus according to another embodiment of the present invention.

DESCRIPTION OF EMBODIMENTS

Figure 1:
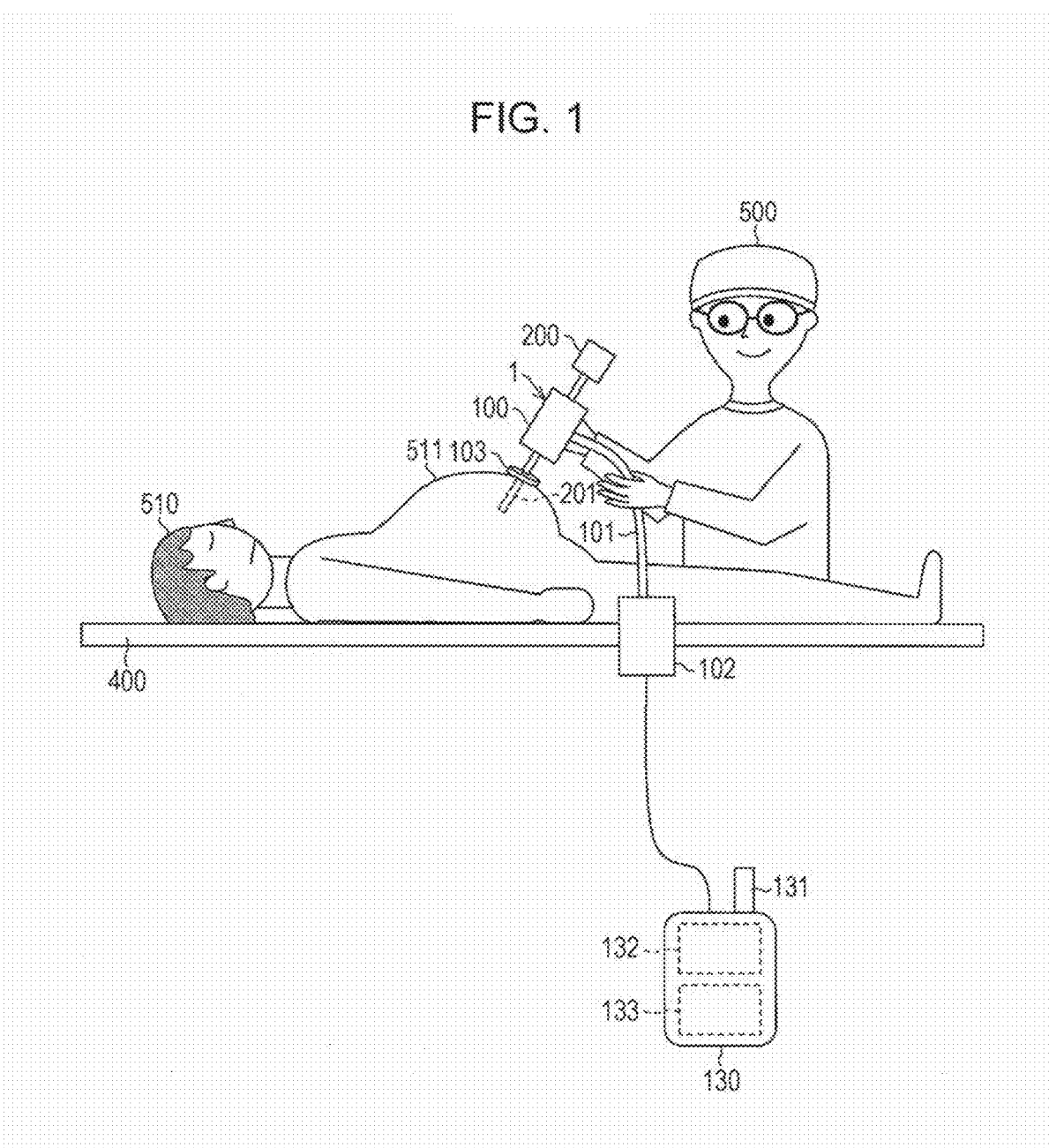
FIG. 1 is a schematic diagram illustrating the schematic configuration of a medical apparatus according to an embodiment of the present invention.

First Embodiment (Overview of Medical Apparatus)
FIG. 1 is a schematic diagram illustrating the schematic configuration of a medical apparatus 1 according to an embodiment of the present invention. In this embodiment, as an example to which the present invention is applied, it is assumed that an insertion section (sheath tube) 201 of a rigid endoscope 200 is inserted into an abdominal cavity of an abdomen 511 of a patient 510 lying on a surgery table 400, and a surgeon 500 performs a surgery based on an image obtained from the rigid endoscope 200.

In FIG. 1, the medical apparatus 1 includes an insertion-section conveying unit 100, a flexible arm (actuator securing unit) 101, a stand (actuator securing unit) 102, a surgical port 103, a control unit (control device) 130, and the rigid endoscope 200. The insertion-section conveying unit 100 and the control unit 130 will be described in detail later. The medical apparatus 1 adjusts the position of the rigid endoscope 200.

The flexible arm 101 supports and secures the insertion-section conveying unit 100 at one end thereof and can be manually bent into a desired shape. Specifically, the flexible arm 101 sets and secures the insertion-section conveying unit 100 at a position desired by the surgeon 500.

The stand 102 secures the other end of the flexible arm 101 so as to secure the flexible arm 101 toward the patient 510 lying on the surgery table 400. The stand 102 is installed (fixed) at the surgery table 400.

The surgical port 103 is a medical instrument having a through-hole for inserting a medical instrument into the abdominal cavity of the patient 510 and is disposed on the surface of the abdomen 511 of the patient 510. The surgical port 103 is not essential depending on the surgical method and is not an essential element of this embodiment.

Although the rigid endoscope 200 having the insertion section 201, which is cylindrical (rod-shaped), is used as an example of a medical instrument in this embodiment, a medical instrument having a rod-shaped (columnar-shaped) insertion section for inserting a medical instrument into the body of the patient 510 may alternatively be used in place of the rigid endoscope 200. For example, a medical instrument having a surgical instrument, such as forceps, provided at the distal end of a columnar insertion section or a rod-shaped catheter also functioning as an insertion section may be used as the medical instrument.

(Configuration of Insertion-Section Conveying Unit)

Figure 2:
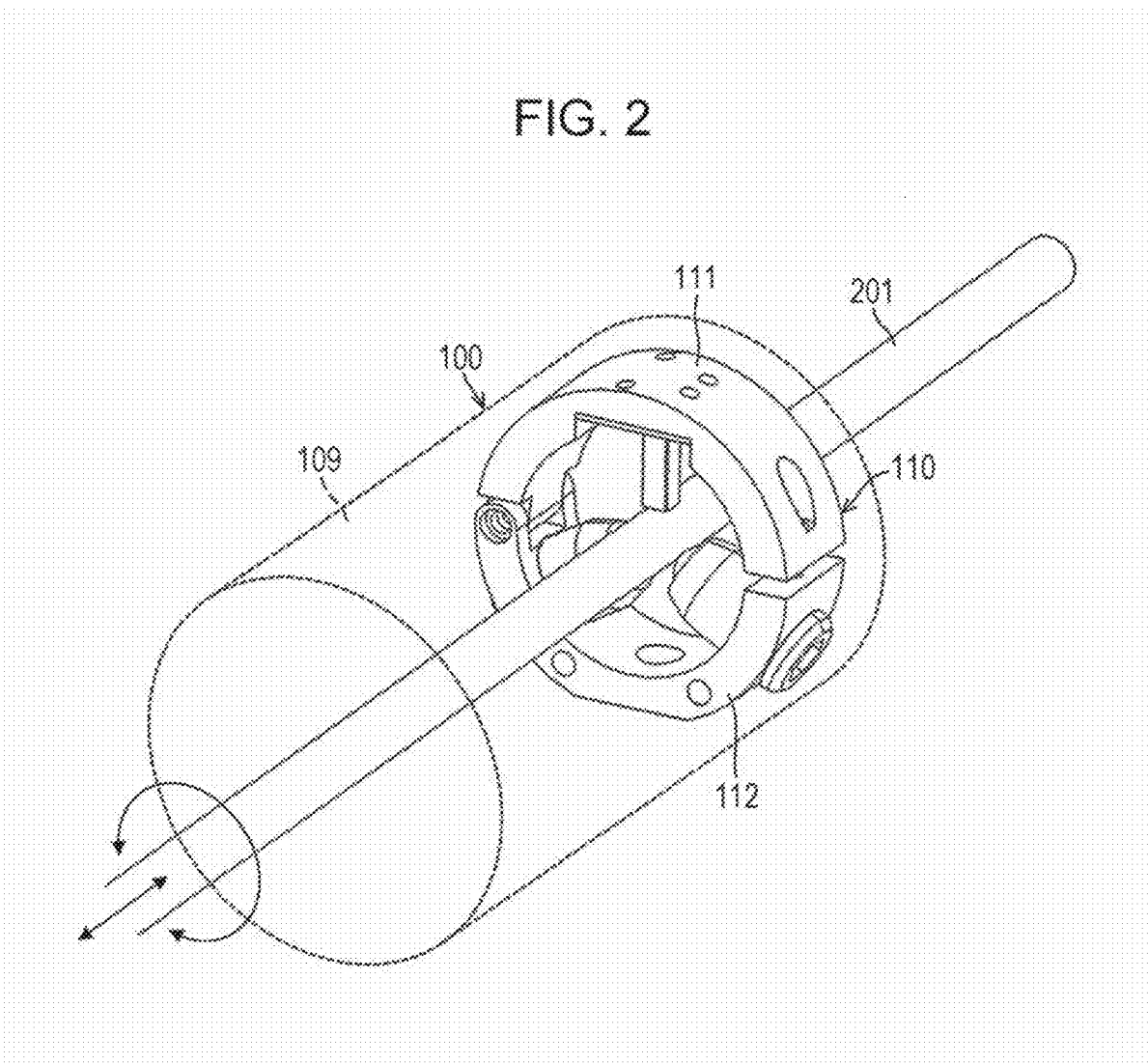
FIG. 2 is a perspective view illustrating the schematic configuration of an insertion-section conveying unit of the medical apparatus.

FIG. 2 is a perspective view illustrating the schematic configuration of the insertion-section conveying unit 100. As shown in FIG. 2, the insertion-section conveying unit 100 includes an actuator holder (actuator securing unit) 109 and an ultrasonic actuator (actuator, friction drive actuator) 110.

The actuator holder 109 is a hollow housing that holds the ultrasonic actuator 110. One end of the flexible arm 101 is secured to a side surface of the actuator holder 109. The actuator holder 109, the flexible arm 101, and the stand 102 constitute an actuator securing unit for securing the ultrasonic actuator 110 to an area near a surgical site.

Figure 3:
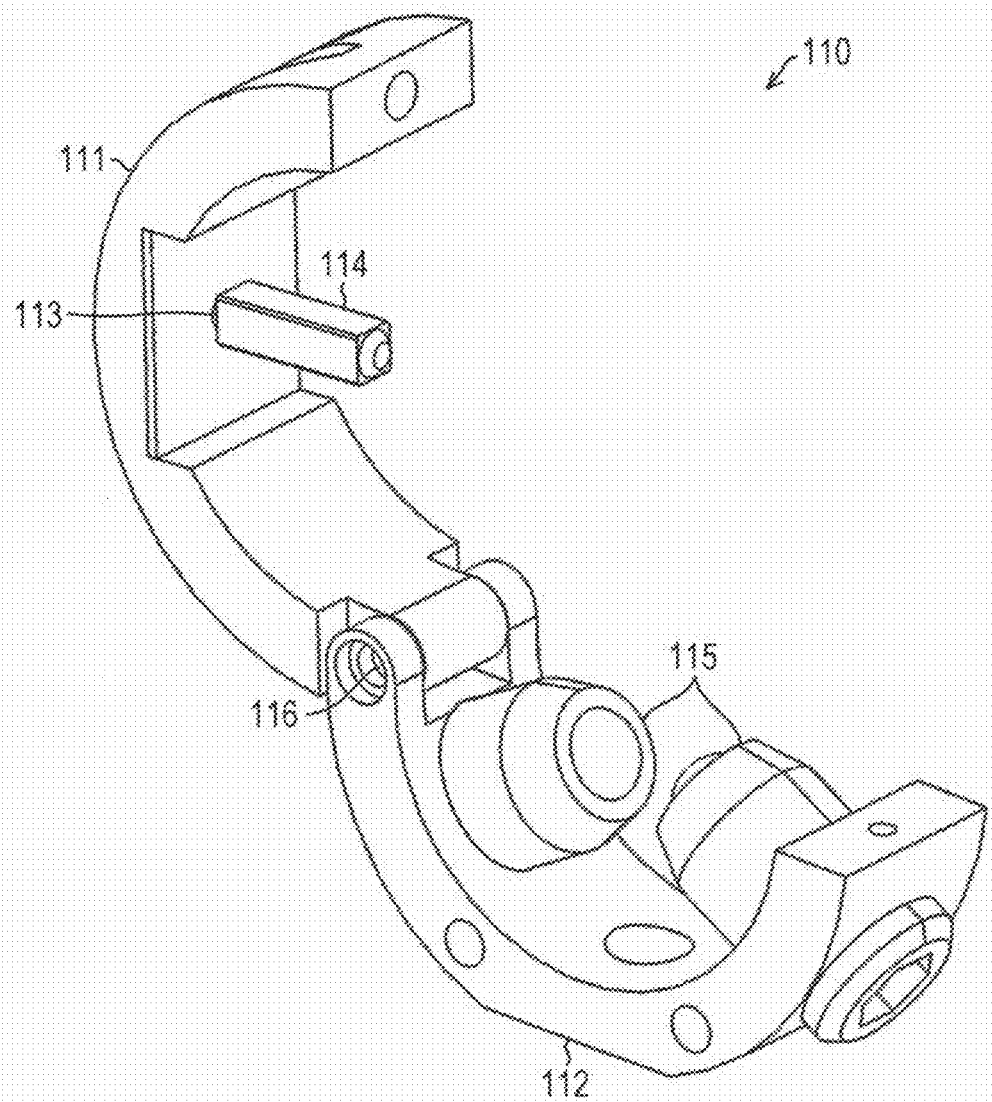
FIG. 3 is a perspective view illustrating the schematic configuration of an ultrasonic actuator of the medical apparatus.

FIG. 3 is a perspective view illustrating the schematic configuration of the ultrasonic actuator 110. As shown in FIG. 3, the ultrasonic actuator 110 includes a housing 111, a housing 112, a stay 113 provided at the inner surface of the housing 111, an ultrasonic vibrator (friction drive element) 114 secured to the housing 111 via the stay 113, and two ball bearings (sliders) 115 secured to the inner surface of the housing 112. The housing 111 and the housing 112 are joined to each other in an openable-closable manner. In a state where the position of the ultrasonic actuator 110 relative to the surgical site within the body cavity is fixed by the actuator holder 109, the ultrasonic actuator 110 conveys the insertion section 201 of the rigid endoscope 200 to an area near the surgical site.

A preload spring (restoring section) 116 applies a restoring force to the housing 111 and the housing 112 in a direction that causes the two housings to close. When closed, the housing 111 and the housing 112 form a ring-shaped housing. When the housing 111 and the housing 112 are closed, the ultrasonic vibrator 114 and the two ball bearings 115 are pressed against the side surface of the insertion section 201 by the restoring force of the preload spring 116. Specifically, the rigid endoscope 200 is held in a direction orthogonal to the axial direction of the insertion section 201 by the ultrasonic vibrator 114 and the two ball bearings 115 (FIG. 2). When the housing 111 and the housing 112 are opened, the distance between the ultrasonic vibrator 114 and the ball bearings 115 increases, so that the insertion section 201 becomes released from the ultrasonic vibrator 114.

The two ball bearings 115 come into point contact with the side surface of the rigid endoscope 200. Therefore, in view of elastic deformation at the contact areas of a protrusion 45 and the two ball bearings 115, at least two restraining areas are required in the direction orthogonal to the axial direction of the insertion section 201 for holding the rigid endoscope 200. For example, one conceivable method for holding the rigid endoscope 200 at other locations thereof involves additionally providing three ball bearings 115 at the inner surface of the actuator holder 109. For simplifying the illustration, the three ball bearings provided at the inner surface of the actuator holder 109 are not shown.

(Configuration of Ultrasonic Vibrator)

Figure 4:
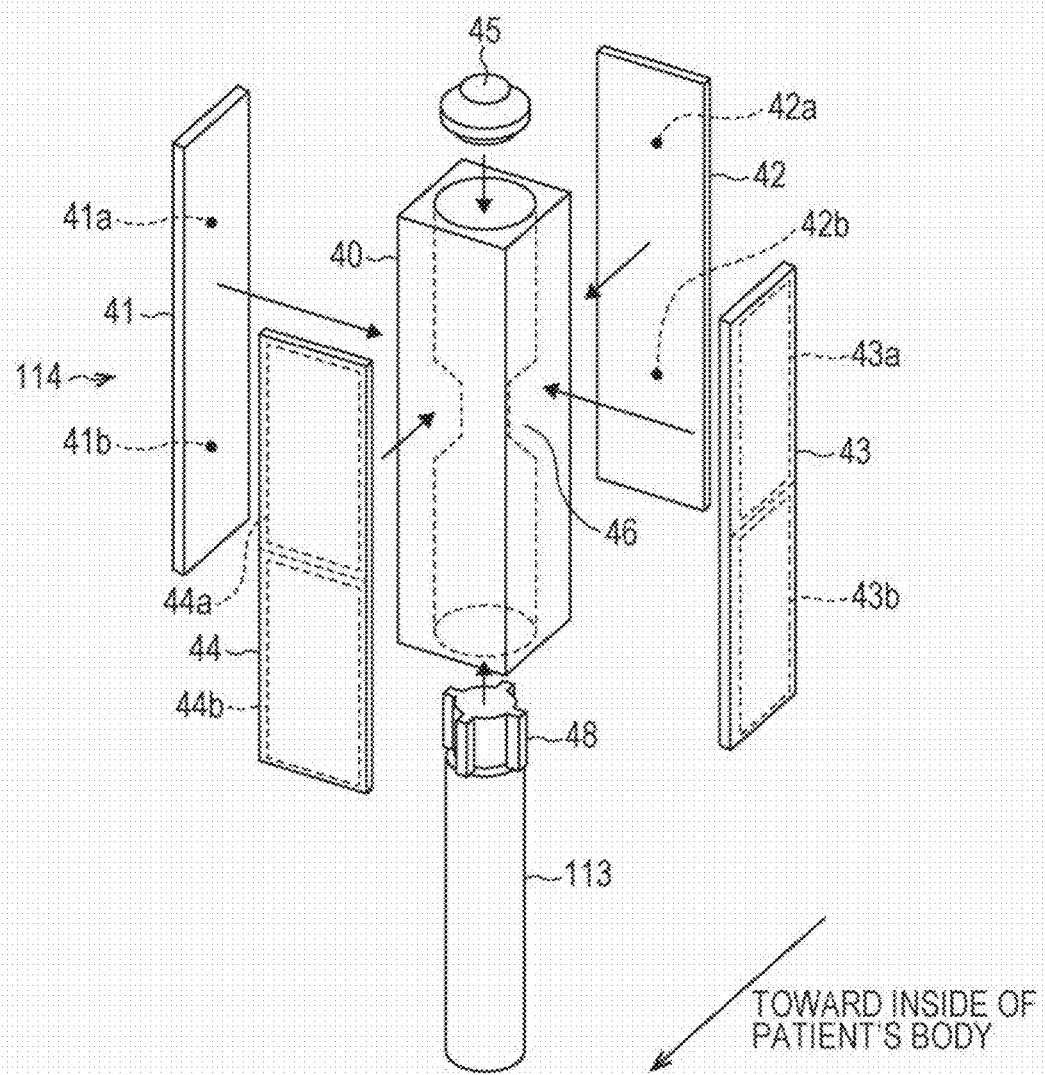
FIG. 4 is a perspective view illustrating the schematic configuration of an ultrasonic vibrator of the ultrasonic actuator.

FIG. 4 is a perspective view illustrating the schematic configuration of the ultrasonic vibrator 114. As shown in FIG. 4, the ultrasonic vibrator 114 includes the stay 113, a vibrating body 40, the protrusion 45, piezoelectric elements 41 to 44, upper electrodes 41*a* to 44*a*, and lower electrodes 41*b* to 44*b*.

The stay (holder) 113 is a rod-shaped member whose distal end is provided with a key 48 for preventing the ultrasonic vibrator 114 from rotating.

The vibrating body 40 is a hollow rectangular column composed of stainless steel and has a substantially square cross-sectional shape. The hollow section (cavity) extends through the vibrating body 40 along the axis of the rod-shaped vibrating body 40. The inner side surface of the vibrating body 40 defining the hollow section is provided with a narrow section 46. The inner side surface of the vibrating body 40 defines a first cavity and a second cavity having a diameter smaller than that of the first cavity.

The narrow section 46 defines the second cavity in the vibrating body 40. In order to prevent the vibrating body 40 from rotating, the narrow section 46 is provided with a key groove having a shape corresponding to that of the distal end of the stay 113. By engaging the key 48 with the key groove, the vibrating body 40 is secured to the housing 111 via the stay 113. This engagement section (narrow section 46) is located at a position that corresponds to two vibration (standing-wave vibration) nodes, which will be described later, so as not to interfere with the vibration.

Although the narrow section 46 is provided near the center of the hollow section of the vibrating body 40 in this embodiment, the position thereof is not limited so long as the narrow section 46 is located at a position where the vibrating body 40 can be secured to the housing 111.

The protrusion 45 is a circular-truncated-cone-shaped member provided at the distal end surface of the vibrating body 40, and an end surface of the protrusion 45 comes into line contact with the side surface of the insertion section 201. For example, the protrusion 45 is composed of brass and has a diameter of 1.8 mm at the bottom surface of the circular truncated cone, a diameter of 0.8 mm at the top surface, and a height of 0.5 mm with respect to the circular truncated cone. However, the shape and the material of the protrusion 45 are not limited to the above. Furthermore, the end surface of the protrusion 45 may be a convex-curved surface such that the protrusion 45 and the insertion section 201 come into point contact with each other.

The distal end of the columnar vibrating body 40 is pressed against the side surface of the columnar insertion section 201 (operation element) via the protrusion 45. The axis (longitudinal direction) of the columnar vibrating body 40 and the axis (longitudinal direction) of the columnar insertion section 201 are orthogonal to each other. The distal end of the vibrating body 40 may be directly brought into contact with the insertion section 201 by omitting the protrusion 45.

The piezoelectric elements 41 to 44 are tabular elements having properties in which a stress change occurs when voltage is applied thereto, and are installed (secured) on the respective side surfaces of the vibrating body 40. The piezoelectric elements 41 to 44 are composed of, for example, a ceramic material or crystal.

The upper electrodes 41a to 44a and the lower electrodes 41b to 44b are installed (secured) on surfaces opposite from the installation surfaces of the piezoelectric elements 41 to 44 relative to the vibrating body 40. The planar upper electrodes 41a to 44a are provided so as to cover the upper halves (the protrusion 45 side relative to the narrow section 46) of the piezoelectric elements 41 to 44. The planar lower electrodes 41b to 44b are provided so as to cover the lower halves of the piezoelectric elements 41 to 44. The upper electrode and the lower electrode provided in each piezoelectric element are disposed side-by-side along the axis (longitudinal direction) of the vibrating body 40. The upper electrode and the lower electrode provided in each piezoelectric element are separated from each other so as not to conduct electricity therebetween.

By supplying the electrodes (the upper electrodes 41a to 44a or the lower electrodes 41b to 44b) with voltage, the areas corresponding to the electrodes in the piezoelectric elements 41 to 44 stretch. This causes the piezoelectric elements 41 to 44 to vibrate. For example, the area corresponding to the upper electrode 41a in the piezoelectric element 41 and the area corresponding to the lower electrode 41b produce different vibrations. Therefore, the upper electrode 41a and the area corresponding to the upper electrode 41a in the piezoelectric element 41 correspond to a first vibration generating element, and the lower electrode 41b and the area corresponding to the lower electrode 41b in the piezoelectric element 41 correspond to a second vibration generating element. Each piezoelectric element may be divided so as to correspond to the upper electrode and the lower electrode.

With regard to wires extending to the electrodes and the control unit 130, which will be described later, it is desirable that the wires be given a waterproof treatment. Since the ultrasonic vibrator 114 deforms at a micro level of ppm, a common waterproof coating technique can be applied.

(Configuration of Control Unit)

As shown in FIG. 1, the control unit 130 includes a command input section 131, a drive signal generator (voltage supplier, operation command section) 132, and a battery 133 that supplies electric power to these components. The control unit 130 is detachably connected to the insertion-section conveying unit 100 by a cable extending via the stand 102 and the flexible arm 101.

The command input section 131 is an input device used by an operator (user) for inputting a command and is, for example, a joystick. For example, the operator manually tilts the joystick forward, rearward, leftward, and rightward so as to input a command for conveying (shifting or rotating) the insertion section 201 of the rigid endoscope 200. The command input section 131 outputs the command input by the operator to the drive signal generator 132. The command input by the operator designates, for example, the moving direction and the moving speed of the insertion section 201.

Based on the command input by the operator, the drive signal generator 132 generates drive signals for causing the piezoelectric elements 41 to 44 to excite desired vibrations and applies the drive signals to the piezoelectric elements. The drive signals are alternating voltages. The drive signal generator 132 sets a phase difference between two drive signals in accordance with the moving direction. The drive signal generator 132 sets the amplitude of the voltage of each drive signal or the duty ratio of the drive signals in accordance with the moving speed.

If the command input by the operator indicates advancing or receding of the insertion section 201, the drive signal generator 132 generates drive signals to be supplied to the electrodes of the piezoelectric elements 42 and 44 that face each other. If the command input by the operator indicates rotation of the insertion section 201, the drive signal generator 132 generates drive signals to be supplied to the electrodes of the piezoelectric elements 41 and 43 that face each other.

(Conveying Principle of Ultrasonic Vibrator)

Next, the conveying principle of the ultrasonic vibrator 114 will be described in detail with reference to FIGS. 5 to 9. For the sake of convenience, the protrusion 45 side and the stay 113 side of the ultrasonic vibrator 114 will be defined as the upper side and the lower side, respectively.

Figure 5:
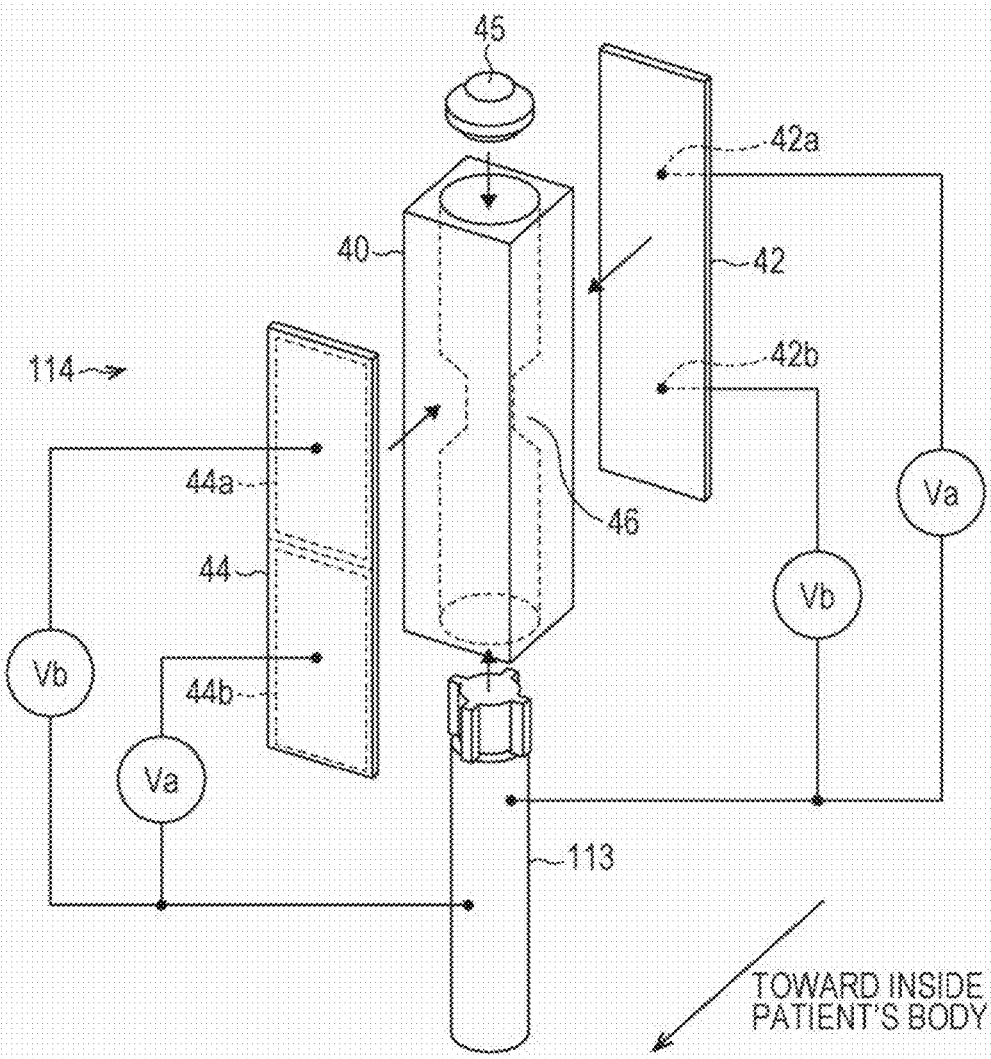
FIG. 5 is an exploded perspective view illustrating the ultrasonic vibrator and voltages supplied thereto.

FIG. 5 is an exploded perspective view illustrating the ultrasonic vibrator 114 and voltages supplied thereto. In FIG. 5, the piezoelectric elements 41 and 43 are not shown for simplifying the illustration. The drive signal generator 132 supplies alternating voltages having different phases to the two electrodes of each of the piezoelectric elements 41 to 44. The drive signal generator 132 fixes the voltage of the stay 113 to a reference voltage (0 V in this case). Since the stay 113, the key 48, and the vibrating body 40 are electric conductors, the vibrating body 40 is fixed to 0 V.

The upper electrode of each piezoelectric element is supplied with the same drive signal as the lower electrode on the opposing piezoelectric element. For example, the upper electrode 42a of the piezoelectric element 42 and the lower electrode 44b of the piezoelectric element 44 are supplied with the same alternating voltage Va. The area corresponding to the upper electrode 42a of the piezoelectric element 42 deforms (stretches) in accordance with the applied voltage Va.

The lower electrode 42b of the piezoelectric element 42 and the upper electrode 44a of the piezoelectric element 44 are supplied with the same alternating voltage Vb. The area corresponding to the lower electrode 42b of the piezoelectric element 42 deforms (stretches) in accordance with the applied voltage Vb.

Figure 6:
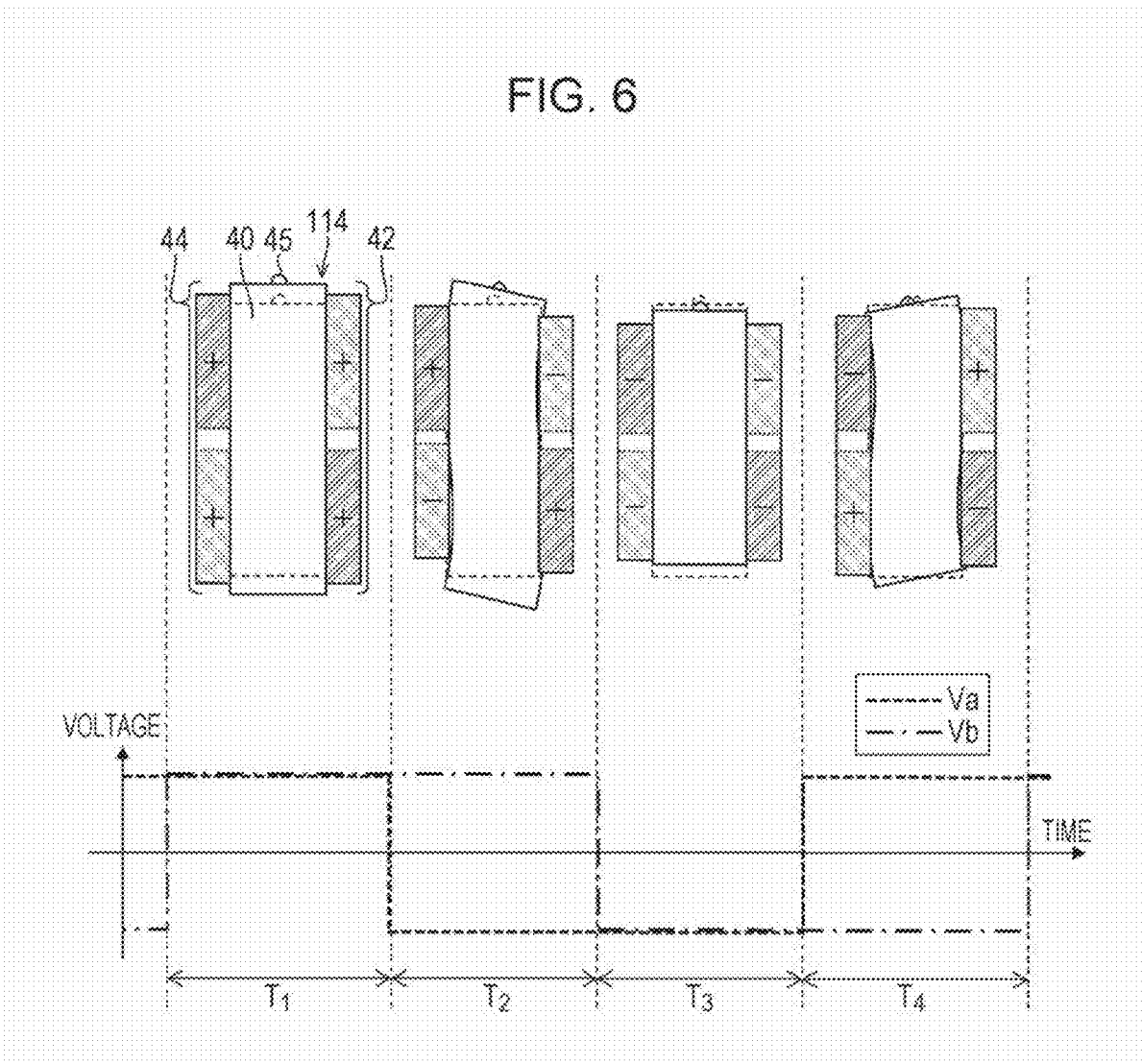
FIG. 6 illustrates alternating voltages and a temporal change of the ultrasonic vibrator.
Figure 7:
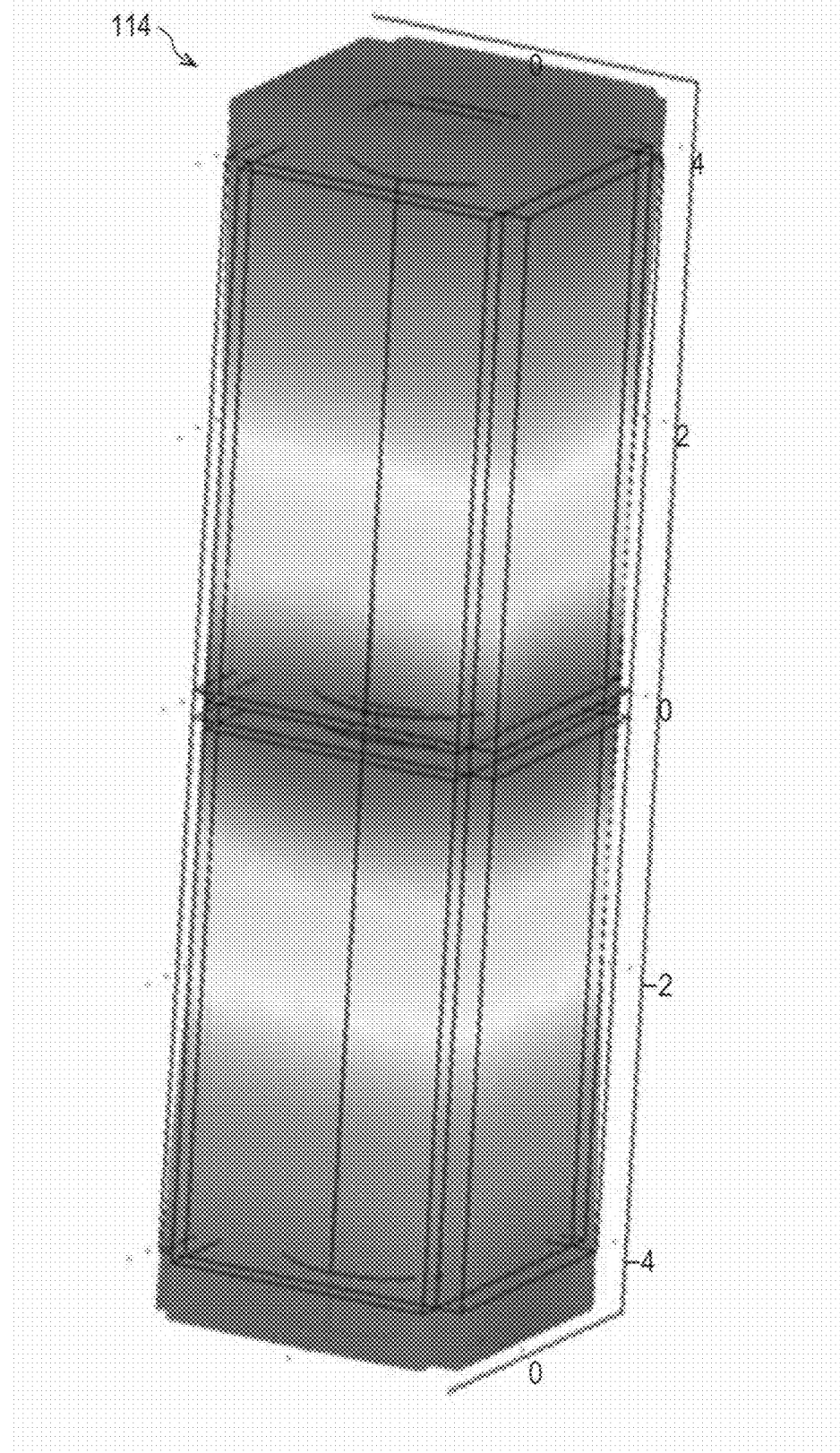
FIG. 7 is a perspective view illustrating a stretching vibration mode of a vibrating body.
Figure 8:
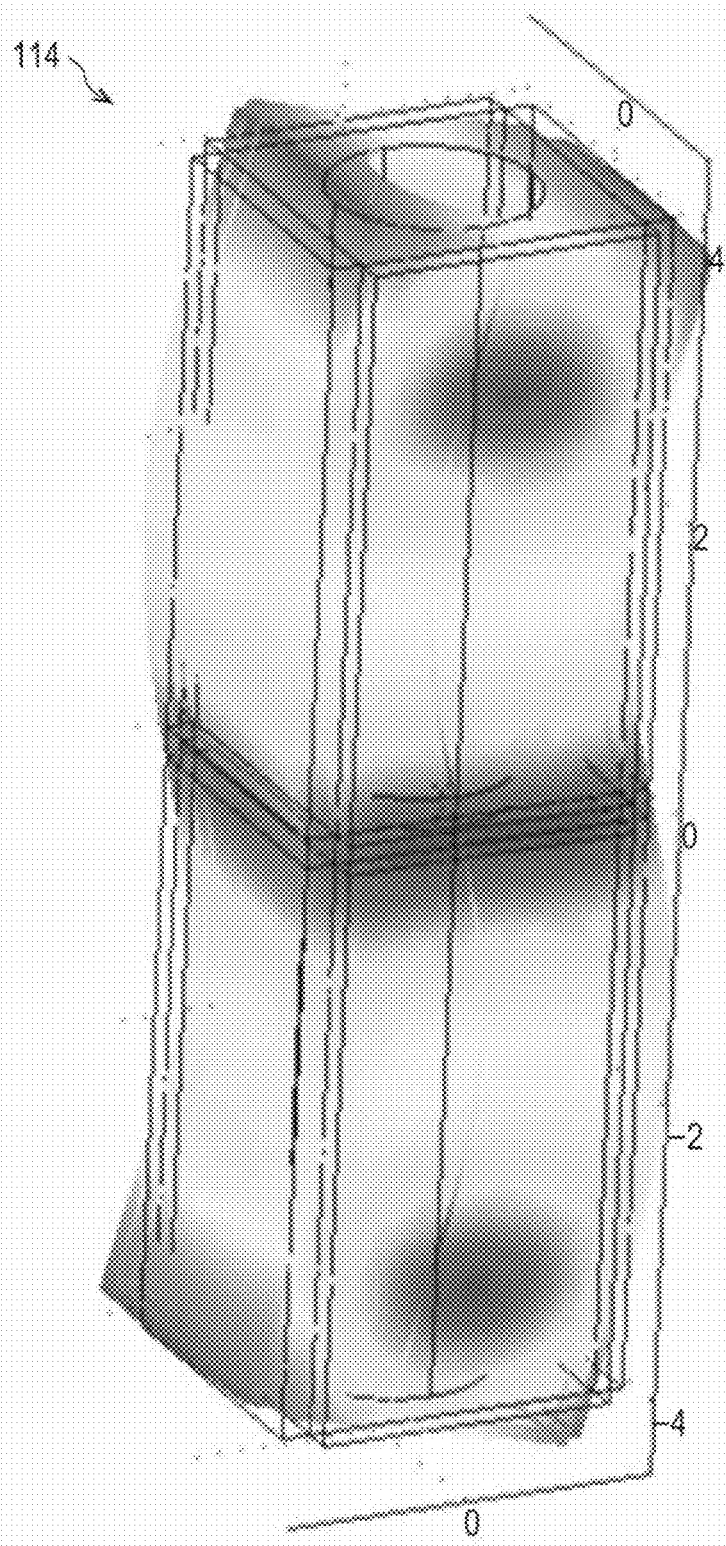
FIG. 8 is a perspective view illustrating a tertiary bending vibration mode of the vibrating body.
Figure 9:
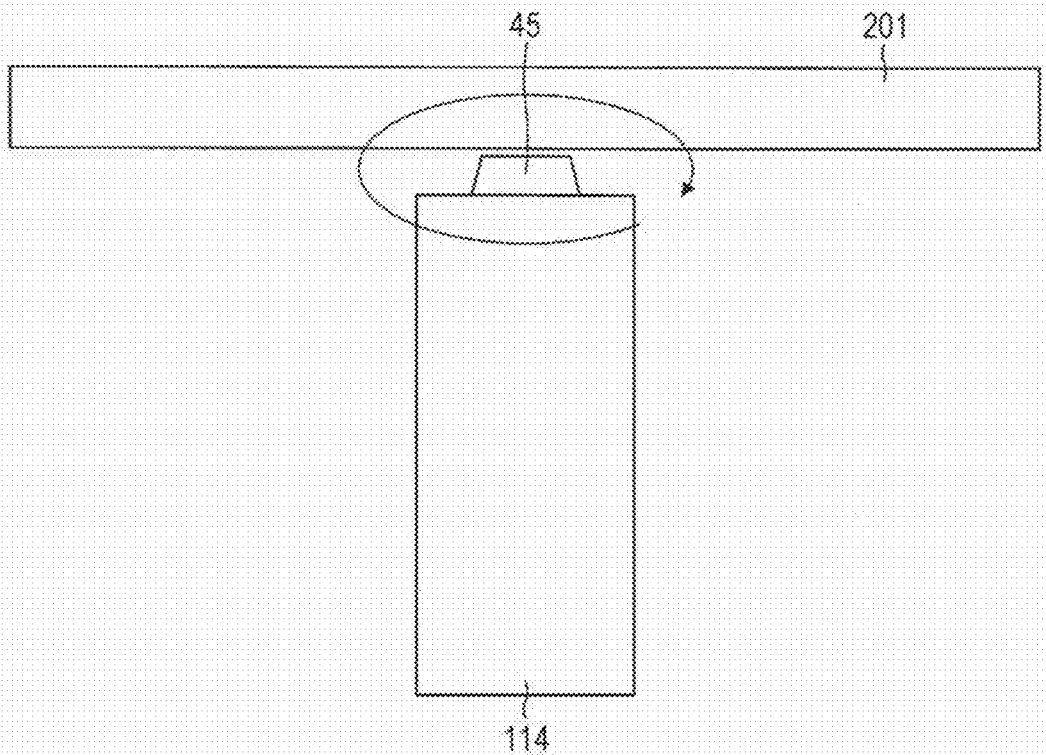
FIG. 9 is a side view illustrating how the vibrating body moves.

FIG. 6 illustrates the alternating voltages Va and Vb and a temporal change of the ultrasonic vibrator 114. The upper side of FIG. 6 illustrates the statuses of the ultrasonic vibrator 114 corresponding to periods T1 to T4. In FIG. 6, the signs (+) and (−) in each of the piezoelectric elements 42 and 44 express areas corresponding to electrodes to which voltages with different polarities are applied. FIG. 7 is a perspective view illustrating a stretching vibration mode L1 of the vibrating body 40. FIG. 8 is a perspective view illustrating a tertiary bending vibration mode B3 of the vibrating body 40. In FIGS. 7 and 8, dark (black) areas indicate areas where there is small deformation in the vibrating body 40, whereas light (white) areas indicate areas where there is large deformation in the vibrating body 40. As shown in FIGS. 7 and 8, the middle of the vibrating body 40 corresponds to a vibration node. FIG. 9 is a side view illustrating how the vibrating body 40 moves.

As shown in FIG. 6, Va and Vb are ±24 V alternating voltages with phases different from each other by 90°. When a positive-polarity voltage is applied to the piezoelectric elements 42 and 44, the piezoelectric elements 42 and 44 are stretched in the direction parallel to the axis of the vibrating body 40 (the direction relative to the insertion section 201). When a negative-polarity voltage is applied to the piezoelectric elements 42 and 44, the piezoelectric elements 42 and 44 are compressed in the direction parallel to the axis of the vibrating body 40. Because the piezoelectric elements 42 and 44 are bonded to the vibrating body 40, the areas corresponding to the piezoelectric elements 42 and 44 in the vibrating body 40 (areas to which the piezoelectric elements are bonded) are similarly stretched/compressed. As a result, in the periods T1 and T3 in which the two alternating voltages Va and Vb have the same polarity, the stretching vibration mode L1 (FIG. 7) of the vibrating body 40 is excited. In the periods T2 and T4 in which the two alternating voltages Va and Vb have different polarities, the tertiary bending vibration mode B3 (FIG. 8) of the vibrating body 40 is excited. If the aspect ratio (width:height) of the vibrating body 40, which is a rectangular column, is 1:4, the resonant frequencies in the stretching vibration mode L1 and the tertiary bending vibration mode B3 substantially match.

With the stretching vibration mode L1 and the tertiary bending vibration mode B3 being excited with the same frequency, the vibrating body 40 deforms as shown in FIG. 6 in one cycle (periods T1 to T4). The excited vibration in each vibration mode is a standing-wave vibration in which the positions of nodes do not change. The narrow section 46 of the vibrating body 40 is located in an area corresponding to a node of the standing-wave vibration (area corresponding to the position between the upper electrodes and the lower electrodes).

In detail, in the period T1, the vibrating body 40 is stretched. The protrusion 45 shifts (linearly moves) toward the insertion section 201. In the period T2, the vibrating body 40 is bent. The protrusion 45 shifts toward the piezoelectric element 42. In the period T3, the vibrating body 40 is compressed. The protrusion 45 shifts away from the insertion section 201. In the period T4, the vibrating body 40 is bent toward the opposite side from the period T2. The protrusion 45 shifts toward the piezoelectric element 44.

As a result, as indicated by an arrow in FIG. 9, the protrusion 45 disposed at the distal end of the vibrating body 40 moves in an elliptic motion. The end surface of the protrusion 45 is pressed against the side surface of the insertion section 201 by the preload spring 116. Therefore, when the alternating voltages Va and Vb are applied to the set of piezoelectric elements 42 and 44, the insertion section 201 of the rigid endoscope 200 is conveyed toward the inside of the patient's body due to friction with the protrusion 45. If the sign of the phase difference between the alternating voltages Va and Vb is reversed, the insertion section 201 is conveyed in the opposite direction. Furthermore, when the alternating voltages Va and Vb are applied to the piezoelectric elements 41 and 43 disposed in the circumferential direction around the axis of the insertion section 201, the insertion section 201 is rotated about that axis. Accordingly, the single ultrasonic vibrator 114 can perform the conveying operation selectively in two directions (the shifting (linearly moving) direction and the rotating direction).

The phase difference between the two alternating voltages Va and Vb sets the moving direction (rotating direction), and the voltage amplitude (or the duty ratio) of the two alternating voltages Va and Vb sets the moving speed (rotating speed). Accordingly, with a drive signal (alternating voltage) generated by the drive signal generator 132, the command from the operator can be reflected as the movement of the rigid endoscope 200.

In this embodiment, the stretching vibration mode L1 and the tertiary bending vibration mode B3 are excited by causing two piezoelectric elements to face each other. Alternatively, for example, similar vibrations may be excited by using the piezoelectric elements 41 and 42 alone. However, since the configuration according to this embodiment has good symmetry, unwanted vibrations other than the stretching vibration mode L1 and the tertiary bending vibration mode B3 are less likely to be excited. Therefore, in this embodiment, high energy efficiency can be achieved.

(Example)

As one example, the vibrating body 40 used is a hollow rectangular column composed of stainless steel and having a square cross section with 2 mm sides and a height of 8 mm. The hollow section has a cylindrical shape with a diameter of 1.6 mm, and the axis of the hollow section and the axis of the rectangular column are aligned with each other. As each of the piezoelectric elements 41 to 44, commercially-available hard PZT (PZT-5H: lead-zirconium-titanium) having a rectangular shape with a thickness of 0.2 mm, short sides of 2 mm, and long sides of 8 mm is used.

As a result, the resonant frequencies in the stretching vibration mode L1 and the tertiary bending vibration mode B3 are both the same at about 280 kHz. Thus, resonance is excited in the ultrasonic vibrator 114, so that conveying (shifting and rotating) of the insertion section 201 is achieved.

(Advantages)

The medical apparatus 1 according to this embodiment can shift the insertion section 201 of the rigid endoscope 200, which is a medical instrument, in the axial direction of the insertion section 201 and can rotate the insertion section 201 about the axis. Since the rigid endoscope 200 can be used to view the insertion section 201 along one side surface thereof, arbitrary areas within the body cavity can be covered in the field of view of the rigid endoscope 200 by using the medical apparatus 1. Consequently, the operator (or the surgeon) can view arbitrary areas within the body cavity through the rigid endoscope 200.

Furthermore, in the medical apparatus 1, the ultrasonic actuator 110 is fixed in position by using the insertion-section conveying unit 100 and the flexible arm 101. The insertion section 201 of the rigid endoscope 200 is driven by the ultrasonic actuator 110 along two axes relative to the ultrasonic actuator 110. Therefore, the space occupied by the medical apparatus 1 can be reduced. Thus, with the medical apparatus 1, a significantly increased working space can be ensured for the surgeon 500, as compared with a medical robotic system in the related art.

For example, in an ultrasonic actuator in the related art in which an operation element is surrounded by a stator, since a through-hole in the stator is in contact with the entire circumference of the operation element, it is necessary to process the operation element and the stator with high precision. Furthermore, in another actuator in the related art that conveys an operation element by using a plurality of rollers, if the operation element is contaminated (with blood, for example), there is a possibility that the frictional force may be uneven among the plurality of rollers. Since this causes the force transmitted to the operation element to become uneven, unexpected operation may possibly occur.

The ultrasonic actuator 110 according to this embodiment is configured to press the distal end (protrusion 45) of the single ultrasonic vibrator 114 against the side surface of the insertion section 201, serving as an operation element, from one direction. Therefore, in the ultrasonic actuator 110, the processing tolerance can be set to a large value. Thus, the ultrasonic actuator 110 can be readily processed and assembled. Moreover, since the ultrasonic vibrator 114 is pressed against the side surface of the insertion section 201 from one direction, an operational failure is less likely to occur even if the insertion section 201 is contaminated.

(Modifications)

In this embodiment, the medical instrument (rigid endoscope 200) is driven by the actuator disposed near the treatment site (the position of the surgical port 103) of the patient 510, so that the space in which, for example, an endoscope operating assistant or a robotic arm in the related art is disposed is reduced. The elements in this embodiment may be replaced, where appropriate, in accordance with the compatibility with the surgical method or the technological development.

For example, although an ultrasonic motor using an ultrasonic vibrator is used as an actuator in this embodiment, an actuator that is driven by, for example, air pressure or an electromagnetic force may be used as an alternative.

Furthermore, with regard to the control unit, the command input section 131 is not limited to a joystick. For example, a semiautomatic controller that sends a command by pointing out an absolute position on a screen and performs an operation on the basis of the position of each site calculated in accordance with the absolute position may be used.

Moreover, the ball bearings 115 may be replaced with sliders, such as fluoroplastic pads, to an extent that the difference in frictional forces does not have an effect on the achievement of the function. Needless to say, for example, the number of sliders, the positions thereof, and the shape thereof are not limited to those in this embodiment so long as they do not interfere with the conveying of the insertion section 201.

The vibrating body 40 is not limited to a rectangular column and may have a columnar shape having at least one side surface (flat surface). A plurality of vibration generating elements may be provided on the one side surface so as to be arranged along the axis (longitudinal direction) of the columnar vibrating body.

The vibration modes utilized as a conveying force of the ultrasonic actuator, the shape of electrodes for exciting the vibration modes, and the applied voltage patterns are changeable, where appropriate, in accordance with the type of medical instrument to be conveyed, and are not limited to those in this embodiment.

In addition to an insertion section of a medical instrument, the ultrasonic actuator 110 can be used for conveying (shifting or rotating) an arbitrary columnar operation element.

Second Embodiment

Figure 10:
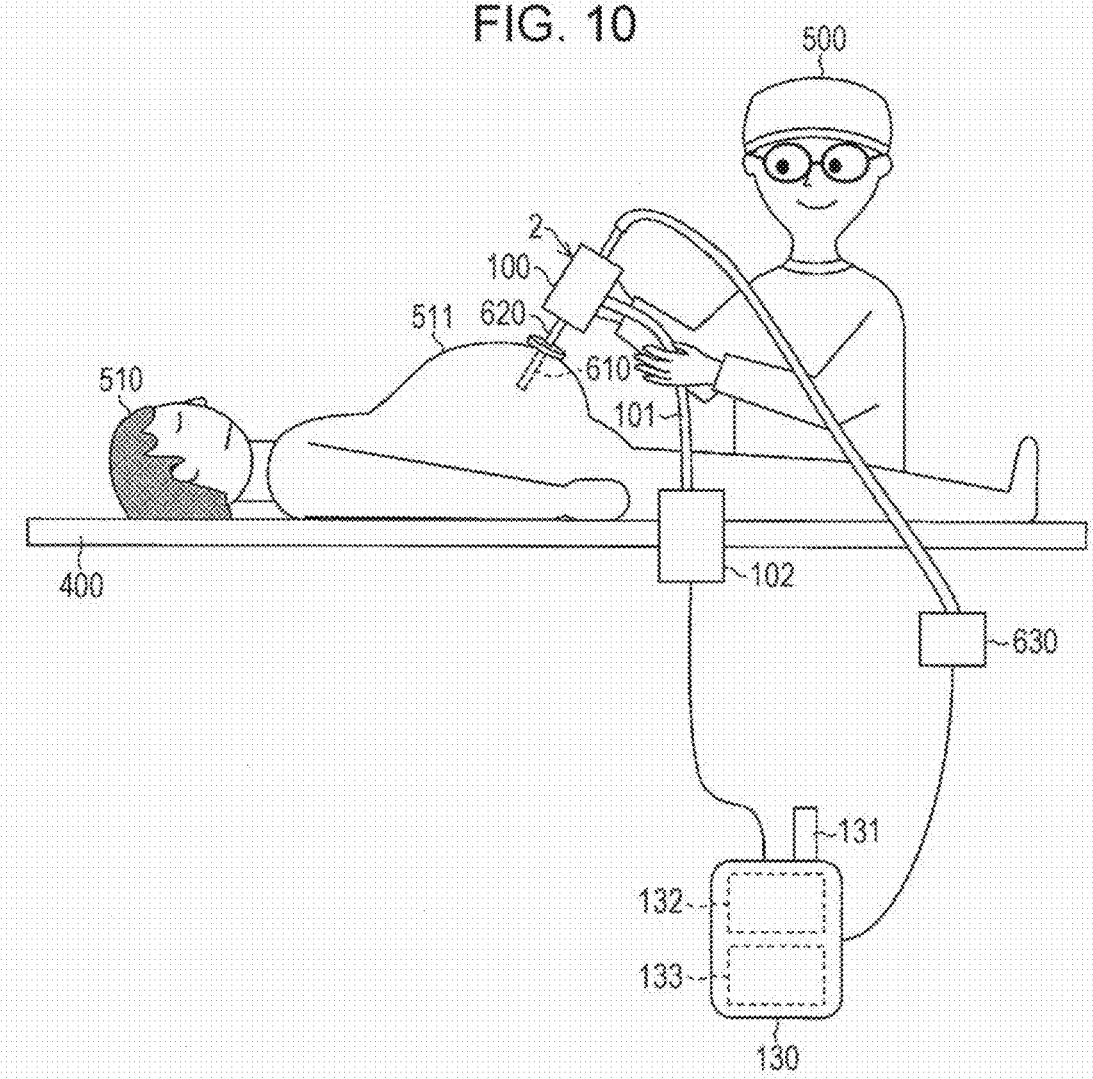
FIG. 10 is a schematic diagram illustrating the schematic configuration of a medical apparatus according to another embodiment of the present invention.
Figure 11:
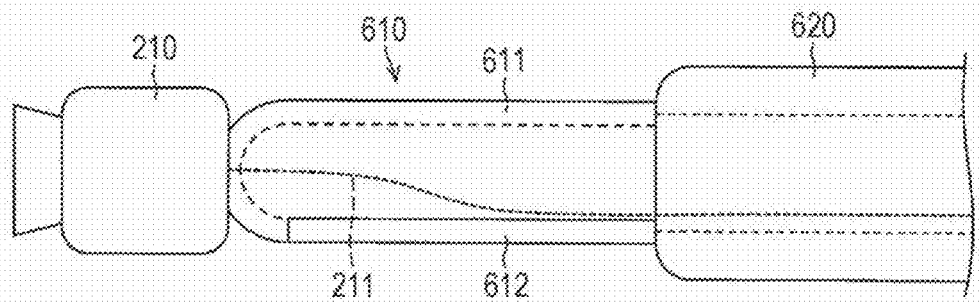
FIG. 11 is a side view illustrating the configuration of a pneumatic actuator of the medical apparatus.
Figure 12:
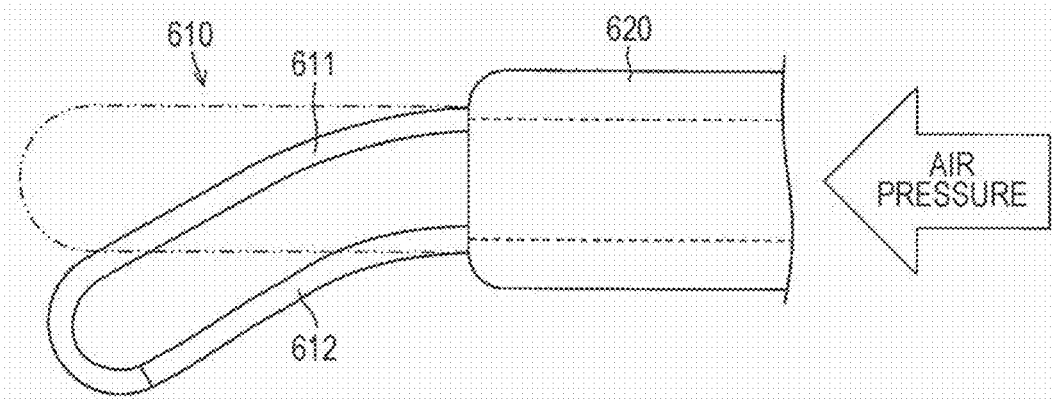
FIG. 12 is a side view illustrating the configuration of the pneumatic actuator of the medical apparatus.

The following description with reference to FIGS. 10 to 12 relates to another embodiment of the present invention. For the sake of convenience, components having identical functions as the components described in the first embodiment will be given the same reference signs, and descriptions thereof will be omitted.

(Overview of Medical Apparatus)

FIG. 10 is a schematic diagram illustrating the schematic configuration of a medical apparatus 2 according to this embodiment. As shown in FIG. 10, the medical apparatus 2 according to this embodiment differs from the medical apparatus 1 according to the first embodiment in using a pneumatic actuator 610 as a medical instrument and in being equipped with an air pump (bend driving device) 630 that bends the pneumatic actuator 610. Furthermore, the medical apparatus 2 according to this embodiment also differs from the medical apparatus 1 according to the first embodiment in that the control unit 130 sends an operation command not only to the ultrasonic actuator but also to the air pump 630.

(Configuration of Insertion Section)

As shown in FIG. 11, the pneumatic actuator 610 in this embodiment includes an expandable tube 611 having a hollow cylindrical shape, a camera 210, and a pipe 620 serving as an insertion section.

The camera 210 is secured to one end of the tube 611. The pipe 620 with the hollow cylindrical shape is connected to the other end of the tube 611 in a communicable manner. Although the tube 611 is an elastic body, a part of the wall surface (lower side in FIG. 11) of the tube 611 has a non-stretching section 612 having higher rigidity than the remaining wall surface. The tube 611 is composed of, for example, silicone.

The camera 210 transmits an image acquired near the surgical site to an image output device (not shown) via a signal wire 211 extending through the tube 611.

The pipe 620 is composed of a rigid material, such as acrylic resin, so that it does not bend even when supplied with air. Furthermore, since the signal wire 211 extends through the hollow section of the pipe 620, the pipe 620 functions not only as an air supply channel but also as a signal-wire storage housing.

The non-stretching section 612 may have stretching properties lower than the other sections of the tube 611 so as to allow the tube 611 to expand at the opposite side of the non-stretching section 612 and to not allow the tube 611 to expand at the non-stretching section 612 side.

The non-stretching section 612 may be formed of non-stretching fiber, such as fiberglass or polyamide fiber, or may be composed of the same silicone as that used for the tube 611.

(Bending Principle of Tube)

The tube 611 is supplied with air from the air pump 630 via the pipe 620, and the side opposite from the non-stretching section 612 side of the tube 611 expands in accordance with an increase in air pressure. In contrast, since the non-stretching section 612 does not expand, the tube 611 bends toward the non-stretching section 612, as shown in FIG. 12.

(Advantages)

Accordingly, in this embodiment, the field of view of the camera 210 can be ensured not only in the axial direction of the pipe 620 (insertion section) and the rotating direction about the axis thereof, but also in the bending direction of the tube 611.

Therefore, the surgeon 500 can observe the surgical site within the body cavity from a larger number of directions, so that a more preferred angle can be selected in the surgical site observation.

(Modifications)

Although the above description of this embodiment relates to an example in which the tube 611 is provided with the non-stretching section 612, this embodiment is not limited to this example. The signal wire 211 may serve as the non-stretching section 612 in a bifunctional fashion. Moreover, the signal wire 211 serving as the non-stretching section 612 in a bifunctional fashion may be secured to the outer side of the tube 611 instead of the inner side thereof.

Third Embodiment

Figure 13:
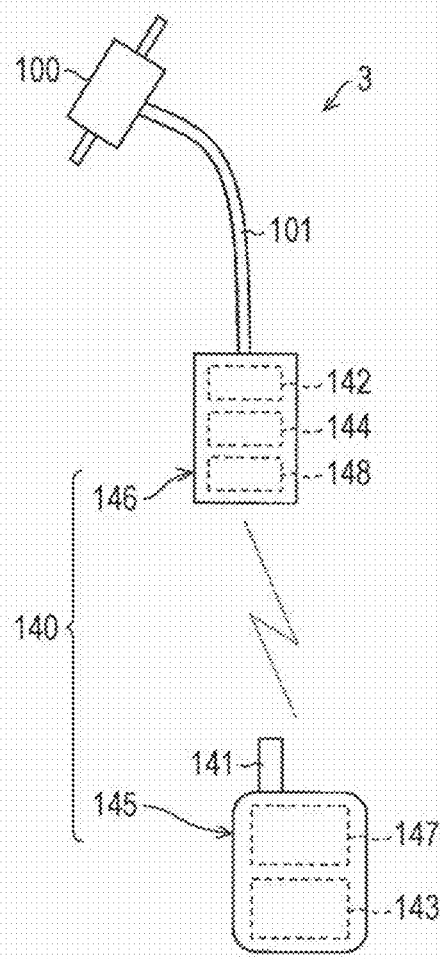
FIG. 13 is a schematic diagram illustrating the schematic configuration of a medical apparatus according to another embodiment of the present invention.

The following description with reference to FIG. 13 relates to another embodiment of the present invention. For the sake of convenience, components having identical functions as the components described in the first and second embodiments will be given the same reference signs, and descriptions thereof will be omitted.

(Overview of Medical Apparatus)

FIG. 13 is a schematic diagram illustrating the schematic configuration of a medical apparatus 3 according to this embodiment. As shown in FIG. 13, the medical apparatus 3 differs from the medical apparatuses according to the first and second embodiments in that the control unit is a wireless control unit 140.

(Configuration of Wireless Control Unit)

As shown in FIG. 13, the wireless control unit 140 includes a main unit 145 and an operation command unit 146.

The main unit 145 includes a command input section 141, a transmitter 147 that transmits a signal corresponding to an amount by which the command input section 141 is operated in the front, rear, left, and right directions, and a first battery (cell) 143 that supplies electric power to these units.

The operation command unit 146 includes a receiver 148, an operation command section 142, and a second battery (cell) 144. The receiver 148 receives a signal transmitted from the transmitter 147. The operation command section 142 generates a drive signal in accordance with the signal received by the receiver 148 and supplies the drive signal to the insertion-section conveying unit 100. The second battery 144 supplies electric power to the receiver 148 and the operation command section 142.

The operation command unit 146 is installed (secured) on the surgery table 400 and has an upper end surface to which one end of the flexible arm 101 is secured. Specifically, the operation command unit 146 also functions as the stand (actuator securing unit) 102 in the first and second embodiments.

The operation command section 142 generates a drive signal corresponding to an alternating voltage in accordance with an operation performed on the command input section 141 by an operator (not shown) and transmits the drive signal to the upper and lower electrodes. Thus, an operation command can be sent to the ultrasonic actuator 110 by wireless communication.

With regard to the wireless control unit 140, the main unit 145 and the operation command unit 146 may sometimes be intervened by an obstacle, such as the surgeon 500. A wireless communication radio wave needs to be in a band that the operator can use freely without a license. Moreover, in view of power consumption, it is desirable that the wireless communication means can be used even when there is an obstacle between wireless communication devices, uses a radio wave in a band that the operator can use freely without a license, and is BT (Bluetooth (registered trademark), which consumes low power.

(Advantages)

Accordingly, in this embodiment, a larger working space can be ensured for the surgeon 500 since an operation command is sent to the ultrasonic actuator by wireless communication. Therefore, the surgeon 500 can perform a medical treatment more smoothly.

Needless to say, the above-described advantage can be realized even when the medical instrument (insertion section) in the first or second embodiment is used.

(Modifications)

In this embodiment, a signal input from an operable section, such as the command input section 141, is transmitted directly to the operation command unit 146 by the main unit 145. However, since the essence of the medical apparatus 3 according to this embodiment is to reflect the information given to the command input section 141 by the operator onto the operation of the ultrasonic actuator by wireless communication, the wireless communication mode is not limited so long as the above essence is achieved.

Fourth Embodiment

Figure 14:
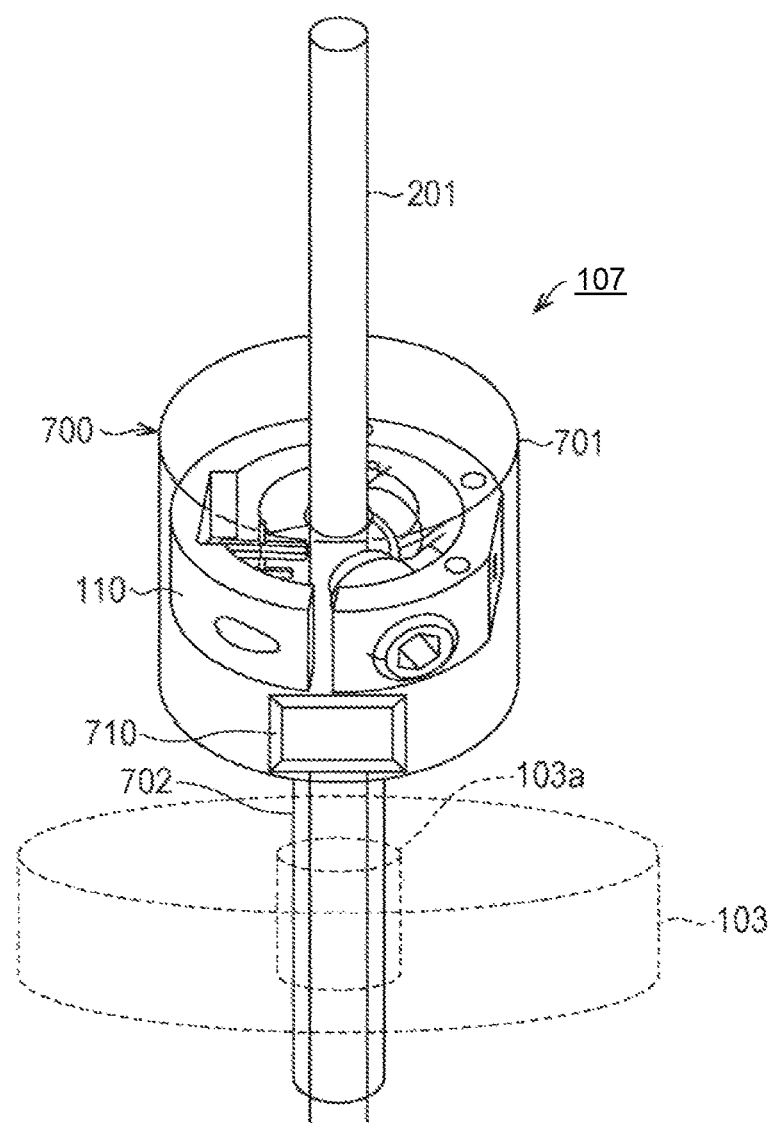
FIG. 14 is a schematic diagram illustrating the schematic configuration of an insertion-section conveying unit according to another embodiment of the present invention.

The following description with reference to FIG. 14 relates to another embodiment of the present invention. For the sake of convenience, components having identical functions as the components described in the first to third embodiments will be given the same reference signs, and descriptions thereof will be omitted.

FIG. 14 is a schematic diagram illustrating the schematic configuration of an insertion-section conveying unit 107 according to this embodiment. As shown in FIG. 14, the insertion-section conveying unit 107 according to this embodiment differs from the insertion-section conveying unit 100 according to the first to third embodiments in that a trocar 700 is used as the actuator holder 109.

(Configuration of Trocar)

The trocar 700 is a medical instrument for inserting a surgical instrument into the body cavity of a patient and is generally used in, for example, surgery that involves the use of a rigid endoscope. Furthermore, as shown in FIG. 14, the trocar 700 includes a tubular trocar housing 701 and a hollow needle 702.

The trocar housing 701 is a hollow housing having a space ensured therein enough for containing the ultrasonic actuator 110 therein. The trocar housing 701 holds the ultrasonic actuator 110.

The needle 702 is a cylindrical component having a hollow section through which the insertion section 201 of, for example, a rigid endoscope, can extend. The outer diameter of the needle 702 is smaller than the diameter of a through-hole 103a of the surgical port 103. One end of the needle 702 is connected to one end of the trocar housing 701 in a communicable manner. The needle 702 is inserted into the surgical port 103 through the through-hole 103a so as to be secured to the surgical port 103. The medical apparatus 3 may additionally include a securing section for securing the trocar 700 to the surgical port 103. For example, the trocar 700 and the surgical port 103 may be provided with engagement sections that correspond with each other.

An external terminal 710 is installed at the side surface of the trocar housing 701. The control unit and the insertion-section conveying unit 107 are electrically connected to each other via the external terminal 710.

The trocar 700 may be of a common type used on the medical front so long as the space ensured in the trocar housing 701 is enough for containing the ultrasonic actuator 110 therein.

(Advantages)

Accordingly, in this embodiment, the trocar 700 is secured to the surgical port 103 so that the ultrasonic actuator 110, which is contained in the trocar housing 701, is fixed in position relative to the surgical site. Therefore, it is not necessary to use the flexible arm 101 and the stand 102, thereby ensuring a larger working space for the surgeon 500. Therefore, the surgeon 500 can perform a medical treatment more smoothly.

Needless to say, the above-described advantage can be realized even when the medical instrument (insertion section) in the first or second embodiment is used.

(Modifications)

The important feature of the insertion-section conveying unit 107 according to this embodiment is that the ultrasonic actuator 110 is secured to the trocar 700 disposed near the surgical site. Therefore, for example, the ultrasonic actuator 110 does not have to be contained in the trocar housing 701. For example, the ultrasonic actuator 110 may be installed at one end of the trocar housing 701.

Furthermore, the surgical port 103 does not necessarily have to be used, and the surgical port 103 can be omitted.

Fifth Embodiment

The following description with reference to FIG. 15 relates to another embodiment of the present invention. For the sake of convenience, components having identical functions as the components described in the first to fourth embodiments will be given the same reference signs, and descriptions thereof will be omitted.

FIG. 15 is a schematic diagram illustrating the schematic configuration of a medical apparatus 4 according to this embodiment. The medical apparatus 4 includes the main unit 145 and the operation command unit 146. As shown in FIG. 15, an insertion-section conveying unit 108 according to this embodiment differs from the insertion-section conveying unit 107 according to the fourth embodiment in that the operation command unit 146 is connected to the side surface of the trocar housing 701 by a connector 730 provided at a side surface of the operation command unit 146.

The operation command unit 146 drives the ultrasonic actuator 110 provided in the trocar 700 based on a command received wirelessly from the main unit 145 of the wireless control unit.

The connector 730 and the operation command unit 146 are detachable from the trocar 700.

(Advantages)

Accordingly, in this embodiment, the operation command unit 146 that has mounted thereon semiconductor components vulnerable to high temperature is removable. Therefore, a sterilization process, specifically, a high-temperature sterilization process such as autoclaving (high-pressure steam sterilization), can be performed on the trocar 700 alone. Consequently, the trocar 700 can be sterilized and cleaned more reliably.

Furthermore, since it is not necessary to take into account the heat resisting properties of the operation command unit 146, generic semiconductor components can be used, whereby the operation command unit 146 can be manufactured at low cost.

Moreover, since an operation command is sent to the ultrasonic actuator 110 by wireless communication, advantages similar to those in the third embodiment can also be achieved in this embodiment.

[Conclusion]

A friction drive actuator (ultrasonic actuator 110) according to a first aspect of the present invention drives a columnar operation element (insertion section 201) and includes a columnar vibrating body (40) having a protrusion at a distal end thereof and a first vibration generating element (piezoelectric elements 41 to 44, upper electrodes 41a to 44a) and a second vibration generating element (piezoelectric elements 41 to 44, lower electrodes 41b to 44b) that are provided at one side surface of the vibrating body. The vibrating body is pressed against a side surface of the operation element via the protrusion.

According to the above-described configuration, the columnar vibrating body is pressed against the side surface of the columnar operation element via the protrusion provided at the distal end of the vibrating body. The first vibration generating element and the second vibration element provided at the side surface of the vibrating body cause the vibrating body to vibrate. With the movement of the distal end of the vibrating body caused by the vibration of the vibrating body, the vibrating body friction-drives the operation element. Because the vibrating body is pressed against the side surface of the operation element via the protrusion, the vibrating body can friction-drive the operation element even in the event of immersion of, for example, a solid or a liquid. Thus, even when the friction drive actuator is contaminated with, for example, extraneous matter, the friction drive actuator can properly drive the operation element. Moreover, the protrusion comes into contact with the side surface of the operation element so that the contact area is reduced, thereby further increasing the resistance to, for example, extraneous matter.

In a friction drive actuator according to a second aspect of the present invention, the vibrating body in the first aspect has a first side surface, a second side surface, a third side surface, and a fourth side surface. The first side surface and the second side surface face each other, the third side surface and the fourth side surface face each other, the first side surface and the third side surface are orthogonal to each other, and the first side surface, the second side surface, the third side surface, and the fourth side surface each have a plurality of vibration generating elements bonded thereto.

According to the above-described configuration, vibration excited in the vibrating body by the plurality of vibration generating elements provided at two opposing side surfaces can cause the operation element to be driven (linearly moved or rotated) in the direction in which the two opposing side surfaces are arranged. Since the first side surface and the third side surface are orthogonal to each other, the friction drive actuator can drive the operation element selectively in two different directions.

In a friction drive actuator according to a third aspect of the present invention, the first vibration generating element and the second vibration generating element in the first aspect are arranged in the longitudinal direction of the vibrating body at the one side surface of the vibrating body.

According to the above-described configuration, the first vibration generating element and the second vibration generating element can cause two different vibration modes to be excited in the vibrating body. Thus, the friction drive actuator can drive the operation element efficiently in accordance with the two different vibration modes.

In a friction drive actuator according to a fourth aspect of the present invention, the vibrating body in the third aspect has a first side surface and a second side surface that face each other, and the second side surface is provided with a third vibration generating element and a fourth vibration generating element. The first vibration generating element and the second vibration generating element are bonded to the first side surface. The third vibration generating element and the fourth vibration generating element are bonded to the second side surface so as to be arranged in the longitudinal direction of the vibrating body.

According to the above-described configuration, the first side surface and the second side surface that face each other each have two vibration generating elements bonded thereto. The two vibration generating elements provided at each side surface are arranged in the longitudinal direction of the vibrating body. Consequently, a desired vibration mode can be efficiently excited, whereby the operation element can be efficiently driven.

In a friction drive actuator according to a fifth aspect of the present invention, each vibration generating element in the fourth aspect includes a piezoelectric element (41 to 44) and a planar electrode (upper electrodes 41a to 44a, lower electrodes 41b to 44b) provided on the piezoelectric element. The first vibration generating element is disposed at the operation element side relative to the second vibration generating element. The third vibration generating element is disposed at the operation element side relative to the fourth vibration generating element. The friction drive actuator further includes a voltage supplier (drive signal generator 132) that supplies a first alternating voltage (Va) to the electrode of the first vibration generating element and the electrode of the fourth vibration generating element and that supplies a second alternating voltage (Vb), having a phase different from that of the first alternating voltage, to the electrode of the second vibration generating element and the electrode of the third vibration generating element.

According to the above-described configuration, in a side view of the vibrating body, a pair of vibration generating elements located at diagonal positions are vibrated in accordance with the same alternating voltage. The two vibration generating elements provided at one side surface are supplied with alternating voltages having different phases. Consequently, a vibration mode that causes the distal end of the vibrating body to move in an elliptic motion can be excited in the vibrating body. Thus, the operation element can be efficiently driven.

In a friction drive actuator according to a sixth aspect of the present invention, the first vibration generating element and the second vibration generating element in the fourth or fifth aspect stretch in a direction parallel to an axis of the columnar vibrating body so as to vibrate the vibrating body.

According to the above-described configuration, the stretching of the first vibration generating element and the second vibration generating element can cause a vibration mode in the axial direction of the columnar vibrating body and a vibration mode that shifts the distal end of the vibrating body in the axial direction of the operation element to be excited in the vibrating body. Thus, the operation element can be efficiently driven.

In a friction drive actuator according to a seventh aspect of the present invention, the friction drive actuator in any one of the first to sixth aspects further includes a slider that slides relative to the side surface of the operation element. The operation element is held by the slider and the vibrating body.

In a friction drive actuator according to an eighth aspect of the present invention, an inner side surface of the columnar vibrating body in any one of the first to seventh aspects defines a cavity extending along an axis of the vibrating body.

According to the above-described configuration, a resonant frequency of the vibrating body can be set in accordance with the cavity. Thus, for example, resonant frequencies of two vibration modes can be readily matched.

In a friction drive actuator according to a ninth aspect of the present invention, the friction drive actuator in the seventh aspect further includes a first housing to which the vibrating body is secured and a second housing to which the slider is secured. When the first housing and the second housing are mutually closed, the vibrating body is pressed against the side surface of the operation element. When the first housing and the second housing are mutually opened, the operation element is released.

According to the above-described configuration, the operation element can be readily attached to and detached from the friction drive actuator. This facilitates the replacement process of the operation element or the cleaning process of the operation element.

In a friction drive actuator according to a tenth aspect of the present invention, the friction drive actuator in the ninth aspect further includes a restoring section that applies a restoring force in a direction that causes the first housing and the second housing to close.

According to the above-described configuration, the restoring force of the restoring section can cause the first housing and the second housing to close and to press the vibrating body against the side surface of the operation element.

In a friction drive actuator according to an eleventh aspect of the present invention, the inner side surface of the vibrating body in the eighth aspect defines a first cavity and a second cavity having a diameter smaller than that of the first cavity.

In a friction drive actuator according to a twelfth aspect of the present invention, the second cavity in the eleventh aspect is located at a position corresponding to a position between the first vibration generating element and the second vibration generating element.

According to the above-described configuration, a node of vibration excited in the vibrating body is located at a position corresponding to the position between the first vibration generating element and the second vibration generating element. Therefore, the second cavity with the small diameter in the vibrating body is located at a position corresponding to a node of vibration. Thus, the second cavity does not interfere with the vibration of the vibrating body.

In a friction drive actuator according to a thirteenth aspect of the present invention, the friction drive actuator in the twelfth aspect further includes a first housing and a holder secured to the first housing. An inner side surface corresponding to the second cavity of the vibrating body and the holder are secured in accordance with a key and a key groove that engage with each other.

According to the above-described configuration, the holder and the vibrating body are secured in accordance with the key and the key groove that engage with each other. Since the inner side surface corresponding to the second cavity of the vibrating body is located at a position corresponding to a node of vibration, the vibrating body can be secured to the first housing without interfering with the vibration of the vibrating body.

The present invention is not limited to the above-described embodiments, and various modifications are possible within the scope defined in the claims. An embodiment obtained by appropriately combining technical means disclosed in the different embodiments is also included in the technical scope of the present invention. Furthermore, by combining the technical means disclosed in the embodiments, a new technical feature can be formed.

INDUSTRIAL APPLICABILITY

The present invention can be used in medical apparatuses. In particular, the present invention can be preferably used in a medical apparatus equipped with, for example, an endoscopic camera, a manipulator, or forceps used in, for example, laparoscopic surgery.

REFERENCE SIGNS LIST 1 to 4 medical apparatus
40 vibrating body
41 to 44 piezoelectric element (vibration generating element)
41a to 44a upper electrode (vibration generating element)
41b to 44b lower electrode (vibration generating element)
45 protrusion
46 narrow section
48 key
100, 107, 108 insertion-section conveying unit
101 flexible arm (actuator securing unit)
102 stand (actuator securing unit)
103 surgical port
109 actuator holder (actuator securing unit)
110 ultrasonic actuator (actuator, friction drive actuator)
111, 112 housing (first housing, second housing)
113 stay (holder)
114 ultrasonic vibrator (vibration generating element)
115 ball bearing (slider)
116 preload spring (restoring section)
130 control unit (control device)
131, 141 command input section
132 drive signal generator (voltage supplier, operation command section)
133, 143, 144 battery (cell)
140 wireless control unit (control device)
142 operation command section
145 main unit
146 operation command unit (actuator securing unit)
147 transmitter
148 receiver
200 rigid endoscope
201 insertion section (operation element)
610 pneumatic actuator
620 pipe (insertion section, operation element)
630 air pump (bend driving device)
700 trocar (actuator securing unit)

The invention claimed is:

1. A friction drive actuator that drives a columnar operation element, the friction drive actuator comprising:
a columnar vibrating body having a protrusion at a distal end thereof; and
a first vibration generating element and a second vibration generating element that are provided at one side surface of the vibrating body,
wherein the vibrating body is pressed against a side surface of the operation element via the protrusion,
further comprising a slider that slides relative to the side surface of the operation element,
wherein the operation element is held by the slider and the vibrating body.

2. The friction drive actuator according to claim 1,
wherein the vibrating body has a first side surface, a second side surface, a third side surface, and a fourth side surface,
wherein the first side surface and the second side surface face each other,
wherein the third side surface and the fourth side surface face each other,
wherein the first side surface and the third side surface are orthogonal to each other, and
wherein the first side surface, the second side surface, the third side surface, and the fourth side surface each have a plurality of vibration generating elements bonded thereto.

3. The friction drive actuator according to claim 1,
wherein the first vibration generating element and the second vibrating generating element are arranged in a longitudinal direction of the vibrating body at the one side surface of the vibrating body.

4. The friction drive actuator according to claim 3,
wherein the vibrating body has a first side surface and a second side surface that face each other, wherein the second side surface is provided with a third vibration generating element and a fourth vibration generating element,
wherein the first side surface has the first vibration generating element and the second vibration generating element bonded thereto, and
wherein the third vibration generating element and the fourth vibration generating element are bonded to the second side surface so as to be arranged in the longitudinal direction of the vibrating body.

5. The friction drive actuator according to claim 4,
wherein each vibration generating element includes a piezoelectric element and a planar electrode provided on the piezoelectric element,
wherein the first vibration generating element is disposed at the operation element side relative to the second vibration generating element,
wherein the third vibration generating element is disposed at the operation element side relative to the fourth vibration generating element, and
wherein the friction drive actuator further comprises a voltage supplier that supplies a first alternating voltage to the electrode of the first vibration generating element and the electrode of the fourth vibration generating element and that supplies a second alternating voltage, which has a phase different from a phase of the first alternating voltage, to the electrode of the second vibration generating element and the electrode of the third vibration generating element.

6. The friction drive actuator according to claim 4,
wherein the first vibration generating element and the second vibration generating element stretch in a direction parallel to an axis of the columnar vibrating body so as to vibrate the vibrating body.

7. The friction drive actuator according to claim 1,
wherein an inner side surface of the columnar vibrating body defines a cavity extending along an axis of the vibrating body.

8. The friction drive actuator according to claim 1, further comprising:
a first housing to which the vibrating body is secured; and
a second housing to which the slider is secured,
wherein the vibrating body is pressed against the side surface of the operation element when the first housing and the second housing are mutually closed, and
wherein the operation element is released when the first housing and the second housing are mutually opened.

9. The friction drive actuator according to claim 7, further comprising:
a restoring section that applies a restoring force in a direction that causes the first housing and the second housing to close.

10. A friction drive actuator that drives a columnar operation element, the friction drive actuator comprising:

a columnar vibrating body having a protrusion at a distal end thereof; and a first vibration generating element and a second vibration generating element that are provided at one side surface of the vibrating body, wherein the vibrating body is pressed against a side surface of the operation element via the protrusion, further comprising a slider that slides relative to the side surface of the operation element, wherein the operation element is held by the slider and the vibrating body, wherein an inner side surface of the columnar vibrating body defines a cavity extending along an axis of the vibrating body, wherein the inner side surface of the vibrating body defines a first cavity and a second cavity having a diameter smaller than a diameter of the first cavity.

11. The friction drive actuator according to claim 10, wherein the second cavity is located at a position corresponding to a position between the first vibration generating element and the second vibration generating element.

12. The friction drive actuator according to claim 11, further comprising:

a first housing; and a holder secured to the first housing, wherein an inner side surface corresponding to the second cavity of the vibrating body and the holder are secured in accordance with a key and a key groove that engage with each other.

* * * * *